United States Patent [19]

Hagemann et al.

[11] 4,298,761
[45] Nov. 3, 1981

[54] PREPARATION OF 4-NITROTHIOANISOLE

[75] Inventors: Hermann Hagemann, Cologne; Erich Klauke, Odenthal; Gerd-Michael Petruck, Bergisch-Gladbach, all of Fed. Rep. of Germany

[73] Assignee: Bayer Aktiengesellschaft, Leverkusen, Fed. Rep. of Germany

[21] Appl. No.: 110,588

[22] Filed: Jan. 9, 1980

[30] Foreign Application Priority Data

Jan. 30, 1979 [DE] Fed. Rep. of Germany ....... 2903505

[51] Int. Cl.$^3$ .......................................... C07C 149/32
[52] U.S. Cl. .................................................... 568/44
[58] Field of Search ...................... 260/609 D, 609 E; 568/44

[56] References Cited

FOREIGN PATENT DOCUMENTS 275037 6/1914 Fed. Rep. of Germany .

OTHER PUBLICATIONS

S. Morris et al., JACS, 68, No. 3 (1946).
Berichte der Deutschen Chemischen Gesellschaft, III, (1909), 3466.
C. C. Price et al., J. Am. Chem. Soc. 68, 498 (1946).
Yagupolski et al., J. Gen. Chem. USSR (1952).
K. Brand, Chem. Ber. 42, 3463 (1909).

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

A process for the preparation of 4-nitrothioanisole comprising successively in a single vessel and without intermediate isolation reacting 4-nitrochlorobenzene with $Na_2S_2$, then with an alkaline $Na_2S$ solution and with a methylating agent. Advantageously the reactions are effected in methanol or aqueous methanol, the reactions with $Na_2S_2$ and $Na_2S$ are carried out at a temperature between about 50° to 70° C., the $Na_2S_2$ is formed in situ in about 20% excess from $Na_2S$ and sulphur, the $Na_2S$ solution is rendered alkaline with sodium methylate or sodium hydroxide, and methylation is effected with methyl chloride at about 27° to 35° C. The product is produced in such high yield and purity that it can be employed directly for chlorination, without extensive purification, to produce insecticide intermediates.

13 Claims, No Drawings

PREPARATION OF 4-NITROTHIOANISOLE

The invention relates to an unobvious process for the preparation of 4-nitrothioanisole.

It is known to prepare 4-nitrothiophenol by reacting 4-nitrochlorobenzene with $Na_2S_2$ and NaOH in accordance with the following equation.

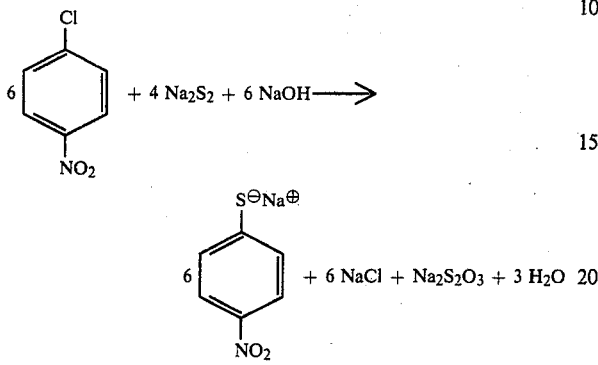

(C. C. Price and G. W. Stacy, J. Am. Chem. Soc. 68, 498 (1946)).

The yields are stated to be 60–65%. Methylating a thiophenolate solution prepared in this way gives, according to Yagupolski and Kiprianov (J. Gen. Chem. USSR, 22, 2273–7 (1952)), a yield of 4-nitrothioanisole of 75% relative to 4-nitrochlorobenzene.

Furthermore, it is known that certain organic disulphides containing nitro groups can also be reduced with $Na_2S$ to the thiophenolates without the nitro group being attacked (K. Brand, Chem. Ber. 42, 3463 (1909)).

Surprisingly, it has now been found that by combining these individual steps, which in themselves are known in principle, a yield of 90% can be achieved in a one-vessel reaction without isolation of intermediate stages.

Accordingly, the invention provides a process for the preparation of 4-nitrothioanisole, which is characterized in that 4-nitrochlorobenzene is successively reacted with $Na_2S_2$, and alkaline $Na_2S$ solution and a methylating agent, in a one-vessel reaction, without isolating the intermediate stages.

The reactions are normally carried out in a polar organic solvent or a polar solvent mixture, for example an alcohol or an aqueous alcohol. Methanol has proved a particularly suitable alcohol.

The temperature of the first two reaction steps should in general be between 40° and 80° C., preferably between 50° and 70° C. In general, a solution of 4-nitrochlorobenzene at about 50° C. is taken and a hot methanolic solution of $Na_2S_2$ (prepared from $Na_2S.3H_2O$ and sulphur) is added; however, the converse procedure can also be followed.

The second reaction step can be carried out by adding a mixture of methanol, $Na_2S.3H_2O$ and methanolic sodium methylate solution. Instead of the sodium methylate solution, a concentrated aqueous solution of an alkali metal hydroxide, especially NaOH, can also be employed.

Furthermore, it has proved advantageous, in order to achieve a good yield, to use an approximately 20% excess of $Na_2S_2$ in the first reaction step. On the other hand, for the second reaction step only approximately stoichiometric amounts are required, in accordance with the following equation:

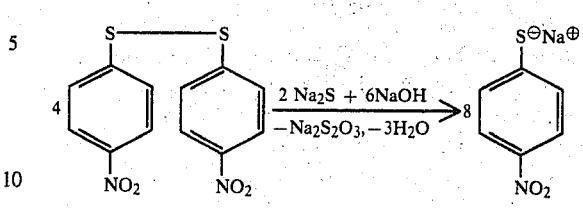

The methylation can, at somewhat above room temperature, be carried out at a satisfactory speed even with the relatively weak methylating agent $CH_3Cl$.

In addition to its low cost and ready availability, methyl chloride offers the advantage, for example compared to dimethyl sulphate, which is usually employed, that it causes less contamination of the effluent. In general, the temperature for the methylation is 27°–35° C.

However, to increase the reaction rate and hence to improve the conversion of methyl chloride, it is of course also possible to work at a higher temperature or under slight excess pressure.

4-Nitrothioanisole is an important intermediate for the preparation of a highly active insecticide of the following structure:

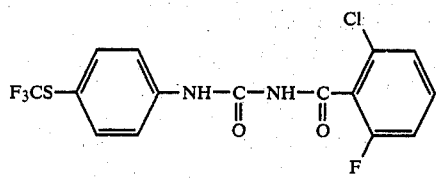

A yield of more than 90% in the preparation of 4-nitrothioanisole is exceptionally advantageous, especially because, if the yield were 75%, as described in the literature, an expensive purification operation would have to be carried out before the next stage, namely the chlorination. In contrast, the 4-nitrothioanisole obtained according to the present process can be chlorinated without further purification.

PREPARATIVE EXAMPLE

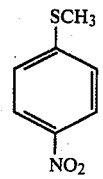

395 g (2.5 mol) of 4-nitrochlorobenzene and 700 ml of methanol were combined and warmed to 50° C. In the course of about 15 minutes, a solution, at 60° C., of 198 g of $Na_2S.3H_2O$ (1.5 mol) and 48 g of sulphur (1.5 mol) in 1,900 ml of methanol was added and the reaction was then allowed to continue for about 2 hours at the reflux temperature.

In the course of about 30 minutes, a solution, again at 60° C., of 208 g of 48% strength NaOH (2.5 mol) and 82.5 g (0.625 mol) of $Na_2S.3H_2O$ in 300 ml of methanol was added drop-wise to the preceding mixture, and the reaction was then allowed to continue for about 1 hour at the reflux temperature.

When the mixture had cooled to 27°–35° C., 250 g (5 mol) of methyl chloride were passed in over the course of 2 hours, the mixture was stirred for a further hour, 2,000 ml of methanol were distilled off in a waterpump vacuum, 2,000 ml of chlorobenzene were added, 2,000 ml of chlorobenzene/$H_2O$/$CH_3OH$ were distilled off in a waterpump vacuum, and the residue was transferred onto a suction filter and separated from the inorganic salts. The filter residue was washed with 150 ml of chlorobenzene, the collected filtrates were concentrated and the residue was distilled. 397 g (94% of theory) of 4-nitrothioanisole (boiling point: 105°–107° C./0.08 mm Hg) were obtained; melting point: 68°–70° C. The non-distillable residue amounted to 9.5 g.

The collected filtrates were directly usable in chlorination without further purification.

It will be appreciated that the instant specification and examples are set forth by way of illustration and not limitation, and that various modifications and changes may be made without departing from the spirit and scope of the present invention.

What we claim is:

1. A process for the preparation of 4-nitrothioanisole comprising successively in a single vessel and without intermediate isolation reacting 4-nitrochlorobenzene with $Na_2S_2$, then with an alkaline $Na_2S$ solution and with a methylating agent.

2. A process according to claim 1, wherein the reactions are carried out in a polar solvent or solvent mixture.

3. A process according to claim 2, wherein the solvent is an alcohol or an aqueous alcohol.

4. A process according to claim 3, wherein the solvent is methanol or aqueous methanol.

5. A process according to claim 1, wherein the reactions with $Na_2S_2$ and $Na_2S$ are carried out at a temperature between about 40° and 80° C.

6. A process according to claim 5, wherein the temperature is between about 50° and 70° C.

7. A process according to claim 1, wherein the first reaction is carried out with about 20% excess $Na_2S_2$.

8. A process according to claim 1, wherein the $Na_2S_2$ is formed in situ from $Na_2S$ and sulphur.

9. A process according to claim 1, wherein the $Na_2S$ solution is rendered alkaline with sodium methylate or sodium hydroxide.

10. A process according to claim 1, wherein methyl chloride is used as the methylating agent.

11. A process according to claim 10, wherein methylation is effected from about 27° to 35° C.

12. A process according to claim 4, wherein the reactions with $Na_2S_2$ and $Na_2S$ are carried out at a temperature between about 50° and 70° C., the $Na_2S_2$ is formed in situ is rendered alkaline with sodium methylate or sodium hydroxide, and methylation is effected with methyl chloride at about 27° to 35° C.

13. In the chlorination of 4-nitrothioanisole wherein 4-nitrochlorobenzene is converted to sodium 4-nitrothiophenolate which is methylated to 4-nitrothioanisole and then chlorinated, the improvement which comprises successively in a single vessel and without intermediate isolation reacting 4-nitrochlorobenzene with $Na_2S_2$, then with an alkaline $Na_2S$ solution and with a methylating agent, whereby the resultant 4-nitrothioanisole can be directly chlorinated without extensive purification.

* * * * *